United States Patent [19]

Hui

[11] Patent Number: 5,401,251
[45] Date of Patent: Mar. 28, 1995

[54] SAFE CAP COVERED INJECTION SYSTEM

[76] Inventor: Allan L. Hui, 363 12th Ave., Apt. #1, San Francisco, Calif. 94118

[21] Appl. No.: 192,358

[22] Filed: Feb. 7, 1994

[51] Int. Cl.⁶ .............................................. A61M 5/32
[52] U.S. Cl. ..................................... 604/192; 604/263
[58] Field of Search ............... 604/192, 198, 110, 263, 604/187

[56] References Cited

U.S. PATENT DOCUMENTS

| | | | |
|---|---|---|---|
| 4,886,503 | 12/1989 | Miller | 604/192 |
| 5,151,089 | 9/1992 | Kirk, III et al. | 604/192 |
| 5,197,954 | 3/1993 | Cameron | 604/110 |

*Primary Examiner*—John D. Yasko

[57] ABSTRACT

A safe cap covered injection system comprising a hollow syringe having a proximal end, a distal end, a reciprocal injector disposed in the proximal end for dispensing fluids from the body upon depression thereof, and a hollow needle coupled at the distal end for injecting fluids from the body; a cover having a hollow interior for the receipt of the needle therein, an aperture sized to allow the passage of the needle therethrough, an opened end located adjacent to the syringe for receiving the distal end thereof, a mechanism for preventing the end of the needle from accidently puncturing an external object; a mechanism for coupling the cover to the distal end of the syringe; and mechanism for placing the needle in shielded orientation with the cover and further allowing the needle to be placed in an opened orientation for use when external reciprocating action is applied to the cover.

2 Claims, 3 Drawing Sheets

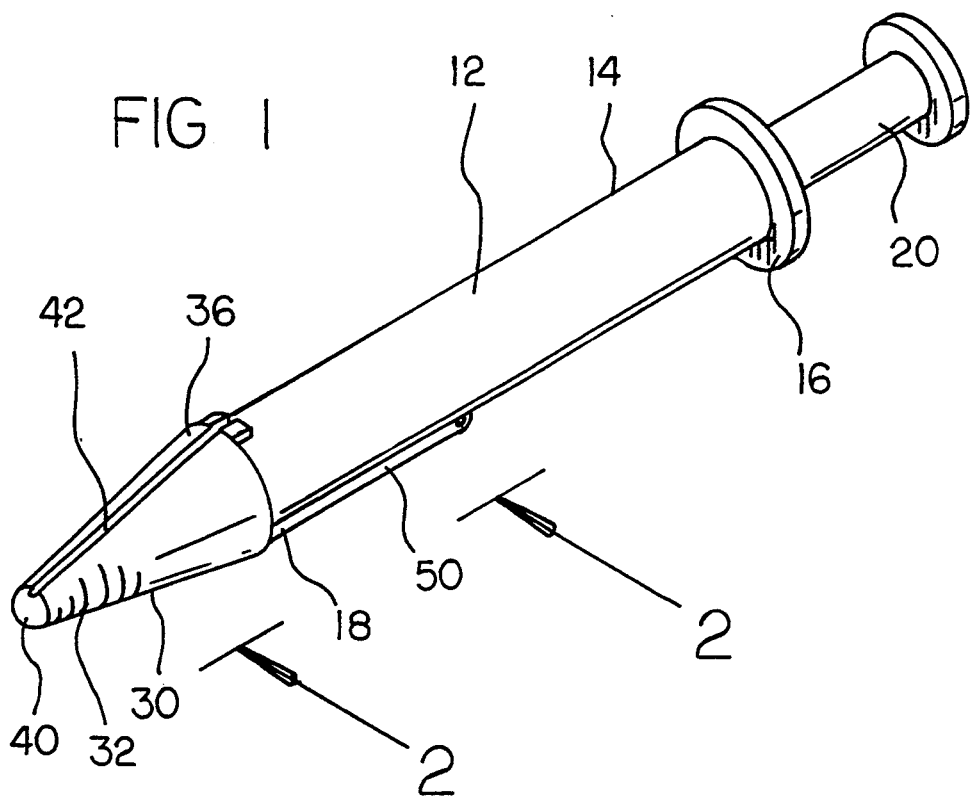
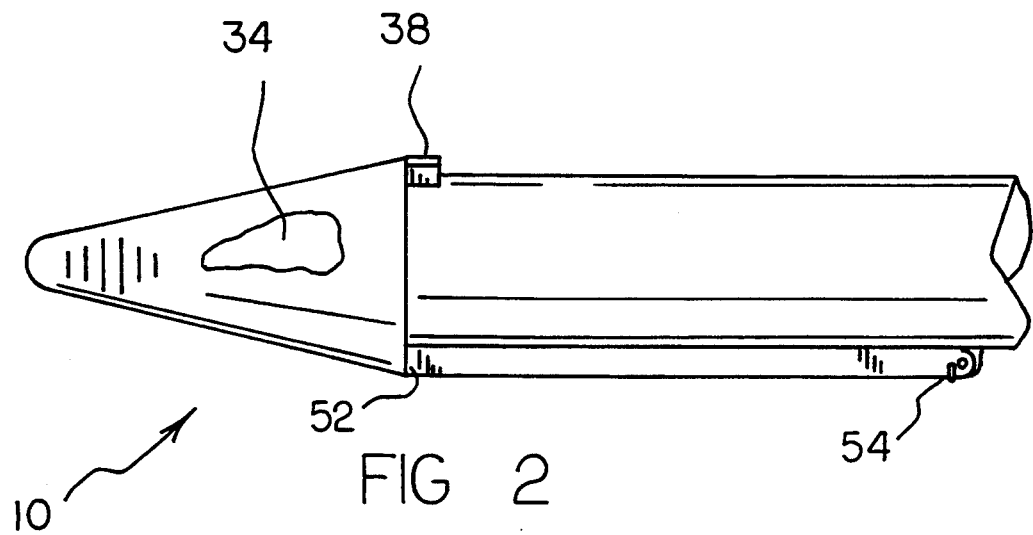

SAFE CAP COVERED INJECTION SYSTEM

BACKGROUND OF THE INVENTION

1. Field of the Invention

The present invention relates to a safe cap covered injection system and more particularly pertains a safe cap covered injection system for automatically covering the needle of a syringe prior to and subsequent to the use of the syringe.

2. Description of the Prior Art

The use of syringes and covers is known in the prior art. More specifically, syringes and covers heretofore devised and utilized for the purpose of covering needles either before or after their use are known to consist basically of familiar, expected and obvious structural configurations, notwithstanding the myriad of designs encompassed by the crowded prior art which have been developed for the fulfillment of countless objectives and requirements.

By way of example, U.S. Pat. Nos. 4,982,842 to Hollister discloses a safety needle container, 5,055,102 to Sitnik discloses swing-away disposable syringe needle cover, 5,135,509 to Olliffe discloses a hypodermic syringe, and 5,139,489 to Hollister discloses a needle protection device.

While these devices fulfill their respective, particular objective and requirements, the aforementioned patents do not describe a safe cap covered injection system having a simple design that further allows the needle to be placed in an opened orientation from the cover for use when external reciprocating action is applied and allows the needle to be placed in a shielded orientation with the cover when external reciprocating action is removed therefrom.

In this respect, the safe cap covered injection system according to the present invention substantially departs from the conventional concepts and designs of the prior art, and in doing so provides an apparatus primarily developed for the purpose of automatically covering the needle of a syringe prior to and subsequent to the use of the syringe.

Therefore, it can be appreciated that there exists a continuing need for new and improved safe cap covered injection system which can be used for automatically covering the needle of a syringe prior to and subsequent to the use of the syringe. In this regard, the present invention substantially fulfills this need.

SUMMARY OF THE INVENTION

In the view of the foregoing disadvantages inherent in the known types of syringes and covers now present in the prior art, the present invention provides an improved safe cap covered injection system. As such, the general purpose of the present invention, which will be described subsequently in greater detail, is to provide a new and improved safe cap covered injection system and method which has all the advantages of the prior art and none of the disadvantages.

To attain this, the present invention essentially comprises a syringe having a hollow cylindrical body having a proximal end, a distal end, a reciprocal injector disposed therein at the proximal end for dispensing fluids from the body upon depression thereof, and a hollow needle coupled at the distal end for injecting fluids from the body; a generally conical shaped cover having an exterior surface with grips disposed thereon to allow a firm grip, a hollow interior for the receipt of the needle therein, a large opened end located adjacent to the distal end of the syringe for receiving the distal end therein, a snap coupled to the cover near the opened end for coupling the cover to the distal end of the syringe, and a closed tip end located remote from and axially aligned with the end of the needle, the tip end adapted to prevent the end of the needle from accidently puncturing an external object, and a slot disposed therealong terminating at the tip end, the slot sized to allow the passage of the needle therethrough; and an elongated extension arm having a distal end secured to the exterior of the cover at a location diametrically opposed to the slot and a proximal end pivotally coupled to the body, the coupling between the body and the extension arm including a spring for resiliently urging the extension arm and cover into a location where the axis of the cover is coextensive with the axis of the body to place the needle in a shielded orientation and further allowing the extension arm to pivot away from the body to place the needle in an opened orientation for use when external reciprocating action is applied to the cover from the finger grips, the cover returning to the shielded orientation once external reciprocating action is removed.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved safe cap covered injection system which has all the advantages of the prior art syringes and covers and none of the disadvantages.

It is another object of the present invention to provide a new and improved safe cap covered injection system which may be easily and efficiently manufactured and marketed.

It is a further object of the present invention to provide a new and improved safe cap covered injection system which is of durable and reliable construction.

An even further object of the present invention is to provide a new and improved safe cap covered injection system which is susceptible of a low cost of manufacture with regard to both materials and labor, and which accordingly is then susceptible of low prices of sale to the consuming public, thereby making such a safe cap covered injection system economically available to the buying public.

Still yet another object of the present invention is to provide a new and improved safe cap covered injection system which provides in the apparatuses and methods of the prior art some of the advantages thereof, while simultaneously overcoming some of the disadvantages normally associated therewith.

Even still another object of the present invention is to provide a new and improved safe cap covered injection system for automatically covering the needle of a syringe prior to and subsequent to the use of the syringe.

Even still another object of the present invention is to provide a new and improved safe cap covered injection system for placing the needle in a shielded orientation with the cover and further allowing the needle to be placed in an opened orientation for use when external reciprocating action is applied to the cover.

Even still another object of the present invention is to provide a new and improved safe cap covered injection system that can be used with only one hand.

Even still another object of the present invention is to provide a new and improved safe cap covered injection system whose cap is an integral part of the system.

Even still another object of the present invention is to provide a new and improved safe cap covered injection system that can be recapped automatically prior to disposal, reducing the possibility of someone accidentally sticking themselves.

Even still another object of the present invention is to provide a new and improved safe cap covered injection system that may be safely utilized by a variety of medical personnel.

Lastly, it is an object of the present invention to provide a new and improved safe cap covered injection system comprising a hollow syringe having a proximal end, a distal end, a reciprocal injector disposed in the proximal end for dispensing fluids from the body upon depression thereof, and a hollow needle coupled at the distal end for injecting fluids from the body; a cover having a hollow interior for the receipt of the needle therein, an aperture sized to allow the passage of the needle therethrough, an opened end located adjacent to the syringe for receiving the distal end thereof, and means for preventing the end of the needle from accidently puncturing an external object; means for coupling the cover to the distal end of the syringe; and means for placing the needle in shielded orientation with the cover and further allowing the needle to be placed in an opened orientation for use when external reciprocating action is applied to the cover.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the new and improved safe cap covered injection system constructed in accordance with the principles of the present invention.

FIG. 2 is a side elevational view of the device taken along the line 2—2 of FIG. 1.

The same reference numerals refer to the same parts through the various Figures.

DESCRIPTION OF THE PREFERRED EMBODIMENT

Figure 3:
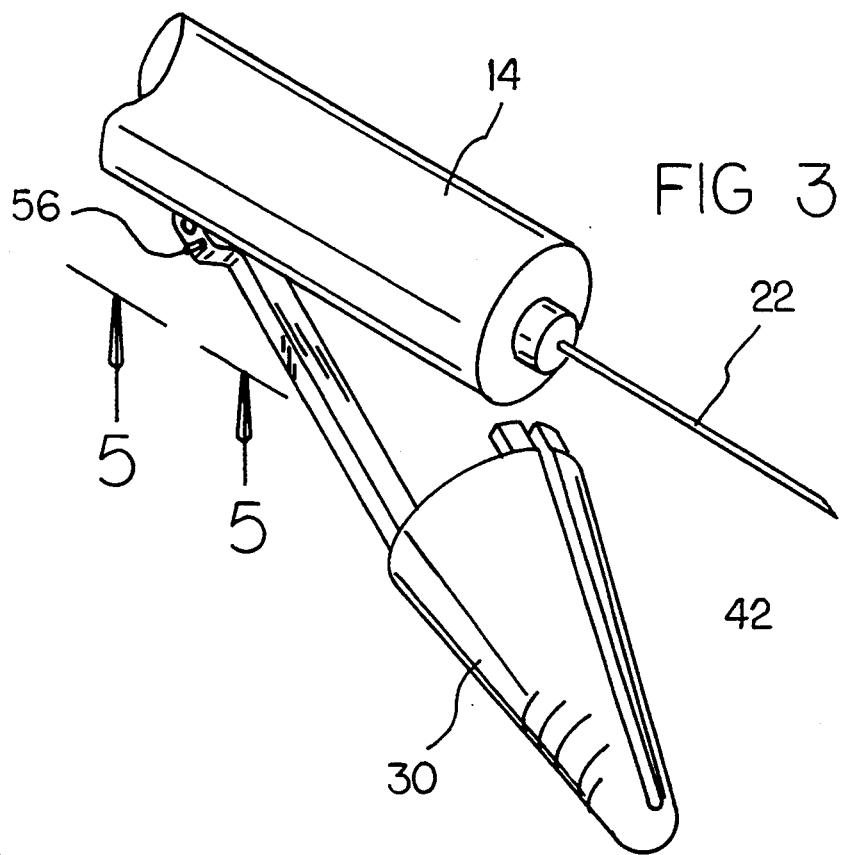
FIG. 3 is a perspective illustration of the distal end of the device of the prior figures but with the cover partially withdrawn.
Figure 4:
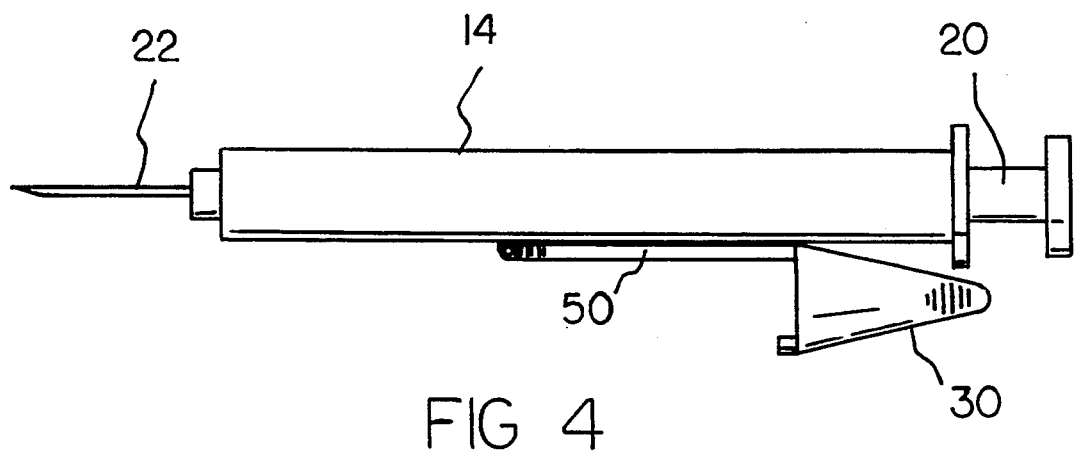
FIG. 4 is a side elevational view of the device of the prior figures with the cover fully retracted and the needle exposed for providing an injection.

With reference now to the drawings, and in particular, to FIG. 1 thereof, the preferred embodiment of the new and improved safe cap covered injection system embodying the principles and concepts of the present invention and generally designated by the reference number 10 will be described.

Specifically, the present invention includes three major components. The major components are the syringe, the cover and the extension arm. These components are interrelated to provide the intended function.

More specifically, it will be noted in the various Figures that the first major component is the syringe 12. The syringe has a hollow cylindrical body 14 for holding fluids. The body of the syringe has a proximal end 16 and a distal end 18. A reciprocal injector 20 is disposed through the proximal end. The injector is used for dispensing fluid from the body upon depression. The syringe includes a hollow needle 22 coupled at the distal end. The needle is used for injecting fluids from the body.

The second major component is a generally conical shaped cover 30. The cover has an exterior surface with grips 32 disposed thereon. The grips are positioned on the cover to allow one a firm grip of the system with only one hand. The cover has a hollow interior 34. The interior is formed to receive a needle 22. The cover includes a large opened end 36 located adjacent to the distal end 18 of the syringe. The opened end is used for receiving the distal end of the syringe therein. The cover also includes a snap 38 coupled to the cover near the opened end. The snap is used to secure the cover over the distal end of the body to seal the needle within the syringe after it has been used. The cover has a closed tip end 40. The tip end is located remote from and axially aligned with the end of the needle. The tip end is adapted to prevent the end of the needle from accidentally puncturing an external object. The cover includes a slot 42 disposed therealong and axially aligned with the needle. The slot extends from the opened end to the tip end. The slot is sized and positioned to allow the passage of the needle therethrough even when the cover is placed close to the distal end of the body.

The third major component is an elongated extension arm 50. The extension arm includes a distal end 52 secured to the exterior of the cover 30 at a location diametrically opposed to the slot. The extension also arm includes a proximal end 54 pivotally coupled to the body 14. The coupling action between the body and the extension arm is supplemented with a spring 56. The spring is used to resiliently urge the extension arm and cover into a location where the axis of the cover is coextensive with the axis of the body. When the spring urges the cover in this position, the needle is allowed to be placed in a shielded configuration. The spring allows the extension arm to pivot away from the body to place the needle in an opened orientation for use when external reciprocating action is applied to the cover from the grips 32. The reciprocating action is applied by the fingers of one hand. Once the external reciprocating action is removed, the spring acts to resiliently urge the cover back to the shielded orientation, thus allowing the needle to be exposed only when it is being actively being utilized for an injection.

Figure 5:
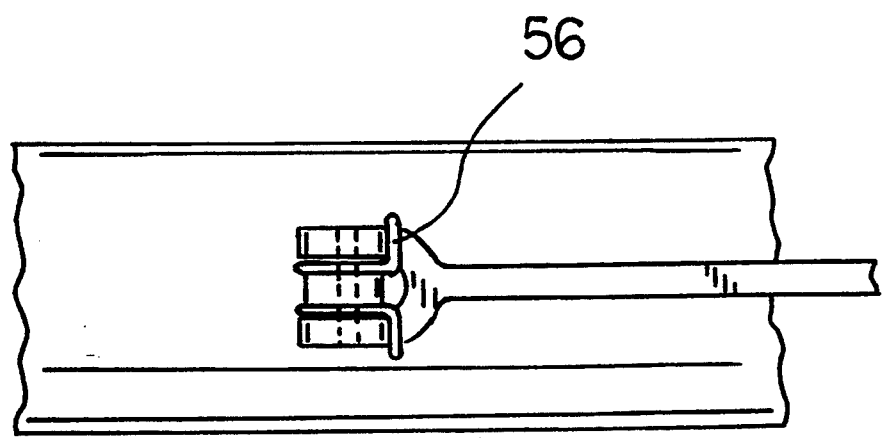
FIG. 5 is an enlarged bottom view of the coupling between the body and the extension arm.

A second embodiment of the present invention is shown in FIG. 5 and includes substantially all of the components of the present invention further including an aperture 60 disposed through the cover. The aperture provides an alternate means of exposing the needle for providing an injection. The cover also includes a safety cap 62. The safety cap is used for sealing the aperture when the needle is not in use.

The safe cap covered injection system is a syringe designed to protect a doctor, nurse, technician or other applicable medical personnel from accidental puncture while also serving as a safe disposal shield. In the preferred embodiment, the body of the syringe is a conventional plastic and features a loaded metal spring located at a position near the lower third of its length. The extension arm is formed of plastic and is constantly spring loaded toward the needle. The distal end of this arm carries a conically shaped plastic cover. This cover has a longitudinally oriented slot formed through the plastic, which is sized just slightly larger than the needle, and two finger grips formed in the plastic cover straddling either side thereof. The slot is terminated just before the end of the cover so that its truncated tip end is blunt and solid. When the arm is released, it will snap into place with the aforementioned slot and blunt the end of the needle. When the syringe is to be used, one simply grasps the finger grips of the cover and rotates the arm 180 degrees to rest against the syringe body. The cover is used as a grip for the fingers while the thumb is positioned on the injector to administer the injection. Upon completion of the injection, the simple expedient of releasing the arm will result in the cover snapping back into place over the needle. The syringe can then be safely disposed. At no time during the injection process is the needle exposed except for the actual administration of the injection. Further, the injection system can then be permanently shielded with the snap to protect those who are obligated to handle injection materials disposed of from hospitals, doctor's offices and the like.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed and desired to be protected by LETTERS PATENT of the United States is as follows:

1. A new and improved safe cap covered injection system comprising, in combination:

a syringe having a hollow cylindrical body having a proximal end, a distal end, a reciprocal injector disposed therein at the proximal end for dispensing fluids from the body upon depression thereof, and a hollow needle coupled at the distal end for injecting fluids from the body;

a generally conical shaped cover having an exterior surface with grips disposed thereon to allow a firm grip, a hollow interior for the receipt of the needle therein, a large opened end located adjacent to the distal end of the syringe for receiving the distal end thereof, a snap coupled to the cover near the opened end for coupling the cover to the distal end of the syringe, and a closed tip end located remote from and axially aligned with the end of the needle, the tip end adapted to prevent the end of the needle from accidently puncturing an external object, and a slot disposed therealong terminating at the tip end, the slot sized to allow the passage of the needle therethrough; and an elongated extension arm having a distal end secured to the exterior of the cover at a location diametrically opposed to the slot and a proximal end pivotally coupled to the body, the coupling between the body and the extension arm including a spring for resiliently urging the extension arm and cover into a location where the axis of the cover is coextensive with the axis of the body to place the needle in a shielded orientation and further allowing the extension arm to pivot away from the body to place the needle in an opened orientation for use when external reciprocating action is applied to the cover from the finger grips, the cover returning to the shielded orientation once external reciprocating action is removed.

2. A safe cap covered injection system comprising:

a hollow syringe having a proximal end, a distal end, a reciprocal injector disposed in the proximal end for dispensing fluids from the body upon depression thereof, and a hollow needle coupled at the distal end for injecting fluids from the body;

a cover having a hollow interior for the receipt of the needle therein, an aperture sized to allow the passage of the needle therethrough, an opened end located adjacent to the syringe for receiving the distal end thereof, and means for preventing the end of the needle from accidently puncturing an external object;

an elongated extension arm secured at one end to the cover and at the other end to an intermediate extent of the syringe for coupling the cover to the distal end of the syringe;

means for placing the needle in shielded orientation with the cover and further allowing the needle to be placed in an opened orientation for use when external reciprocating action is applied to the cover; and an aperture disposed through the cover to allow the needle to pass therethrough and a safety cap for sealing the aperture when the needle is not in use.

* * * * *